United States Patent [19]
Serafini et al.

[11] Patent Number: 6,114,152
[45] Date of Patent: Sep. 5, 2000

[54] METHODS FOR MAKING NUCLEIC ACIDS

[75] Inventors: Tito Serafini, San Francisco; Percy Luu, Oakland; John Ngai; David Lin, both of Berkeley, all of Calif.

[73] Assignee: The Regents of the University of California, Oakland, Calif.

[21] Appl. No.: 09/049,806

[22] Filed: Mar. 27, 1998

Related U.S. Application Data

[60] Provisional application No. 60/069,589, Dec. 12, 1997.

[51] Int. Cl.[7] .................................................... C12P 19/34
[52] U.S. Cl. .............................................................. 435/91.2
[58] Field of Search ................................ 435/91.2, 91.3, 435/91.1, 91.5, 91.51, 91.52; 536/23.1, 24.3, 24.1

[56] References Cited

U.S. PATENT DOCUMENTS

| | | | |
|---|---|---|---|
| 4,952,496 | 8/1990 | Studier et al. | 435/91 |
| 5,514,545 | 5/1996 | Eberwine | 435/6 |

OTHER PUBLICATIONS

Lin et al., NAR 29 (21) : 4954–4960, 1993.
Brady et al, Methods in Mol. & Cell. Biol. 2:17–25, 1990.
Toellner KM et al.: "The use of reverse transcription polymerase chain reaction to analyse large numbers of mRNA species from a single cell" Journal of Immunological Methods, vol. 191, 1996, pp. 71–75.

*Primary Examiner*—George C. Elliott
*Assistant Examiner*—Melissa Schmidt
*Attorney, Agent, or Firm*—Richard Aaron Osman

[57] ABSTRACT

Nucleic acids are made by adding a known nucleotide sequence to the 3' end of a first RNA having a known sequence at the 5' end to form a second RNA and reverse transcribing the second RNA to form a cDNA. In one embodiment, the first RNA is an amplified mRNA, the known sequence at the 5' end comprises a poly(T) sequence, the adding step comprises using a polyadenyltransferase to add a poly(A) sequence to the 3' end, the reverse transcribing step is initiated at a duplex region comprising the poly(T) sequence hybridized to the poly(A) sequence, the cDNA is converted to double-stranded cDNA by a polymerase initiating from a noncovalently joined duplex region, and the double-stranded cDNA is transcribed to form one or more third RNAs.

21 Claims, 2 Drawing Sheets

METHODS FOR MAKING NUCLEIC ACIDS

CROSS REFERENCE TO RELATED APPLICATION

This application claims priority to U.S. Provisional Application No. 60/069589 filed Dec. 12, 1997 by Tito Serafini, Percy Luu, John Ngai and David Lin and entitled methods for Amplifying Nucleic Acids.

The disclosed inventions were made with Government support under Grant (Contract) Nos. GM07048, 1RO1DC02253 and 5F32DC00193-03 awarded by the National Institutes of Health. The government may have rights in these inventions.

INTRODUCTION

1. Field of the Invention

The field of this invention is making nucleic acids.

2. Background

The ability to characterize cells by gene expression provides a wide variety of applications in therapy, diagnostics and bio/medical technology. However, in many of these application, the starting or source material such as stem cells, cancerous cells, identified neurons, embryonic cells, etc. is highly limiting, making it necessary to amplify the targeted mRNA populations. Two existing methods for amplifying mRNA populations suffer from significant limitations. One method, the Brady and Iscove method (Brady et al., 1990, Methods Mol & Cell Biol 2, 17–25), produces only short (200–300 bp), extreme 3' fragments of mRNAs using a PCR-based method which exponentially amplifies artifacts. A second method, the Eberwine protocol (Eberwine et al. (1992) Proc. Natl. Acad. Sci USA 89, 3010–3014) provides sequential linear amplification steps and is the current method of choice for amplifying m'NA populations from limiting material. Nevertheless, this protocol suffers from a number of deficiencies. For example, the amplified product does not represent full-length aRNA for many endogenous mRNAs, and hence the method is of limited use for generating probes or cDNA libraries.

Relevant Literature

Sippel (1973) Eur. J. Biochem. 37, 31–40 discloses the characterization of an ATP:RNA adenyltransferase from *E. coli* and Wittmann et al. (1997) Biochim. Biophys. Acta 1350, 293–305 disclose the characterization of a mammalian poly(A) polymerase. Gething et al. (1980) Nature 287, 301–306 disclose the use of an ATP:RNA adenyltransferase to polyadenylate the '3 termini of total influenza virus RNA. Eberwine et al. (1996) U.S. Pat. No.5,514,545 describes a method for characterizing single cells based on RNA amplification Eberwine et al. (1992) Proc. Natl. Acad. Sci USA 89, 3010–3014, describe the analysis of gene expression in single live neurons. Gubler U and Hoffman B J. (1983) Gene (2–3), 263–9, describe a method for generating cDNA libraries, see also the more recent reviews, Gubler (1987) Methods in Enzymology, 152, 325–329 and Gubler (1987) Methods in Enzymology, 152, 330–335. Clontech (Palo Alto, CA) produces a "Capfinder" cloning kit that uses "GGG" primers against nascent cDNAs capped with by reverse transcriptase, Clontechnitques 11, 2–3 (October 1996), see also Maleszka et al. (1997) Gene 202, 39–43.

SUMMARY OF THE INVENTION

The invention provides methods and compositions for making nucleic acids. The general methods comprise the steps of adding a known nucleotide sequence to the 3' end of a first RNA having a known sequence at the 5' end to form a second RNA and reverse transcribing the second RNA to form a cDNA. According to one embodiment, the first RNA is an amplified mRNA, the known sequence at the 5' end comprises a poly(T) sequence, the adding step comprises using a polyadenyltransferase to add a poly(A) sequence to the 3' end, and the reverse transcribing step is initiated at a duplex region comprising the poly(T) sequence hybridized to the poly(A) sequence. The resultant cDNA transcript may be single-stranded, isolated from the second RNA and optionally converted to double-stranded cDNA, preferably by a DNA polymerase initiating at a noncovalently joined duplex region. The cDNA may also be transcribed to form one or more third RNAs. In another embodiment, the first RNA is made by amplifying a mRNA by the steps of hybridizing to the poly(A) tail of the mRNA a poly(T) oligonucleotide joined to an RNA polymerase promoter sequence, reverse transcribing the mRNA to form single-stranded cDNA, converting the single-stranded cDNA to a double-stranded cDNA and transcribing the double-stranded cDNA to form the first RNA.

DETAILED DESCRIPTION OF PREFERRED EMBODIMENTS OF THE INVENTION

The following preferred embodiments and examples are offered by way of illustration and not by way of limitation.

Figure 2:
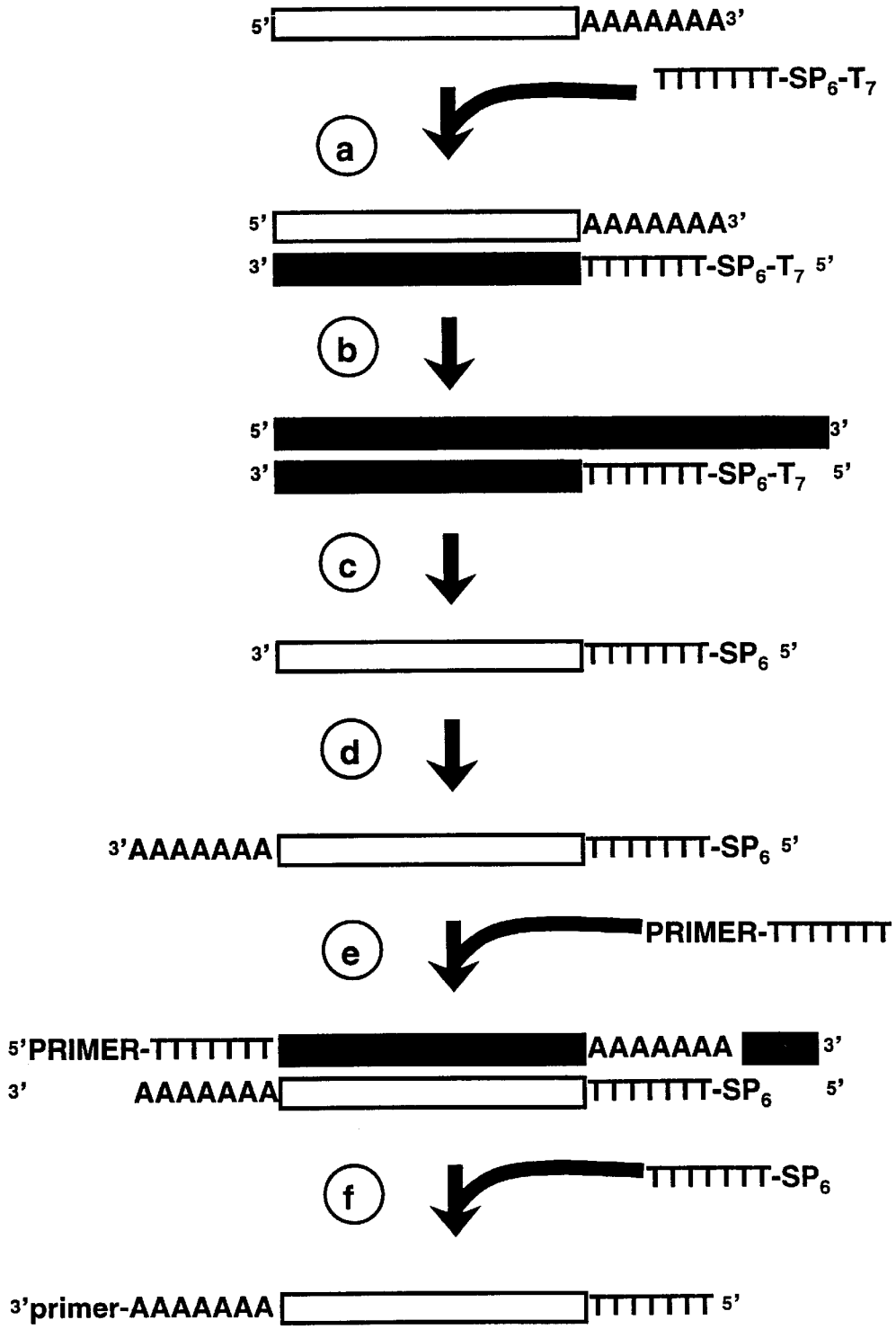
FIG. 2 is a schematic of another embodiment of the invention using a second promoter sequence.

The general methods comprise the steps of adding a known nucleotide sequence to the 3' end of a first RNA having a known sequence at the 5' end to form a second RNA and reverse transcribing the second RNA to form a cDNA. The known sequence at the 5' end of the first RNA species is sufficient to provide a target for a primer and otherwise determined largely by the nature of the starting material. For example, where the starting material is mRNA, the known sequence at the 5' end may comprise a poly(A) sequence and/or (b) an internal mRNA sequence of an mRNA. Alternatively, where the starting material is amplified RNA, or aRNA, the known sequence may comprise a poly(T) sequence or the complement of a known internal mRNA sequence. The known 5' sequence may advantageously comprise additional sequences such as primer target sites, RNA polymerase sites, etc. For example, the presence of both a primer target site such as a poly(T) sequence and an RNA polymerase promoter sequence permits enhanced opportunities for downstream amplification or transcription (see FIG. 2 and related text below).

The adding step may be effect by any convenient method. For example, a polyadenyltransferase or poly(A) polymerase may be used to add selected nucleotides to the 3' end. Poly(A) polymerases may be derived from a wide variety of prokaryotic and eukaryotic sources, are commercially available and well-characterized. In another example, a ligase may be used to add one or more selected oligonucleotides. These enzymes are similarly readily and widely available from a wide variety of sources and are well characterized.

The added known 3' sequence is similarly sufficient to provide a target for a primer, otherwise the nature of the added known sequence is a matter of convenience, limited only by the addition method. For example, using ligase mediated oligonucleotide addition, essentially any known sequence that can be used as target for a primer may be added to the 3' end. With polyadenyltransferase mediated addition, it is generally more convenient to add a poly(N) sequence, with many such transferases demonstrating optimal efficiency when adding poly(A,) sequence. Fore polyadenyltransferase mediated additions, the added sequence will generally be in the range of 5 to 50 nucleotides, preferably in the range of 6 to 25 nucleotides, more preferably in the range of 7 to 15 nucleotides.

The reverse transcribing step is initiated at a noncovalently joined duplex region at or near the '3 end of the second RNA species (the first species with the added 3' sequence), generally formed by adding a primer having sufficient complementarity to the 3' end sequence to hybridize thereto. Hence, where the 3' end comprises a poly(A) sequence, the reverse transcribing step is preferably initiated at a duplex region comprising a poly(T) sequence hybridized to the poly(A) sequence. For many applications, the primer comprises additional functional sequence such as one or more RNA polymerase promoter sequences such as a T,7 or T3 RNA polymerase promoter, one or more primer sequences, etc.

In a preferred embodiment, the RNA polymerase promoter sequence is a T7 RNA polymerase promoter sequence comprising at least nucleotides −17 to +6 of a wild-type T7 RNA polymerase promoter sequence, preferably joined to at least 20, preferably at least 30 nucleotides of upstream flanking sequence, particularly upstream T7 RNA polymerase promoter flanking sequence. Additional downstream flanking sequence, particularly downstream T7 RNA polymerase promoter flanking sequence, e.g. nucleotides +7 to +10, may also be advantageously used. For example, in one particular embodiment, the promoter comprises nucleotides −50 to +10 of a natural class III T7 RNA polymerase promoter sequence. Table 1 provides exemplary promoter sequences and their relative transcriptional efficiencies in the subject methods (the recited promoter sequences are joined to a 23 nucleotide natural class III T7 promoter upstream flanking sequence).

TABLE I

Transcriptional efficiency of T7 RNA polymerase promoter sequences.

| Promoter Sequence | Transcriptional Efficiency |
|---|---|
| T AAT ACG ACT CAC TAT AGG GAG A (SEQ ID NO: 1, class III T7 RNA polymerase promoter) | ++++ |
| T AAT ACG ACT CAC TAT AGG CGC (SEQ ID NO: 2, Eberwine et al. (1992) supra) | + |
| T AAT ACG ACT CAC TAT AGG GCG A (SEQ ID NO: 3, Bluescript, Stratagene, La Jolla, CA) | + |

The transcribed cDNA is initially single-stranded and may be isolated from the second RNA by any of wide variety of established methods. For example, the method may involve treating the RNA with a nuclease such as RNase H, a denaturant such as heat or an alkali, etc., and/or separating the strands electrophoretically. The second strand cDNA synthesis may be effected by a number of well established techniques including 3'-terminal hairpin loop priming or methods wherein the polymerization is initiated at a noncovalently joined duplex region, generated for example, by adding exogenous primer complementary to the 3' end of the first cDNA strand or in the course of the Hoffman-Gubler protocol. In this latter embodiment, the cDNA isolation and conversion to double-stranded cDNA steps may be effected together, e.g. contacting the RNA with an RNase H and contacting the single-stranded cDNA with a DNA polymerase in a single incubation step. In any event, these methods can be used to construct cDNA libraries from very small, e.g. single cell, starting materials.

In a particular embodiment, the methods further comprise the step of repeatedly transcribing the single or double-stranded cDNA to form a plurality of third RNAs, in effect amplifying the first RNA species. Preferred transcription conditions employ a class III T7 promoter sequence (SEQ ID NO: 1) and a T7 RNA polymerase under the following reaction conditions: 40 mM Tris pH 7.9, 6 mM $MgCl_2$, 2 mM Spermidine, 10 mM DTT, 2 mM NTP (Pharmacia), 40 units RNAsin (Promega), 300–1000 units T7 RNA Polymerase (6.16 Prep). The enzyme is stored in 20 mM HEPES pH 7.5, 100 mM NaCl, 1 mM EDTA, 1 mM DTT and 50% Glycerol at a protein concentration of 2.5 mg/mL and an activity of 300–350 units/uL. In exemplary demonstrations, 1–3 uL of this polymerase was used in 50 uL reactions. Starting concentrations of template can vary from picogram quantities (single cell level) to 1 ug or more of linear plasmid DNA. The final NaCl concentration is preferably not higher than 6 mM.

Figure 1:
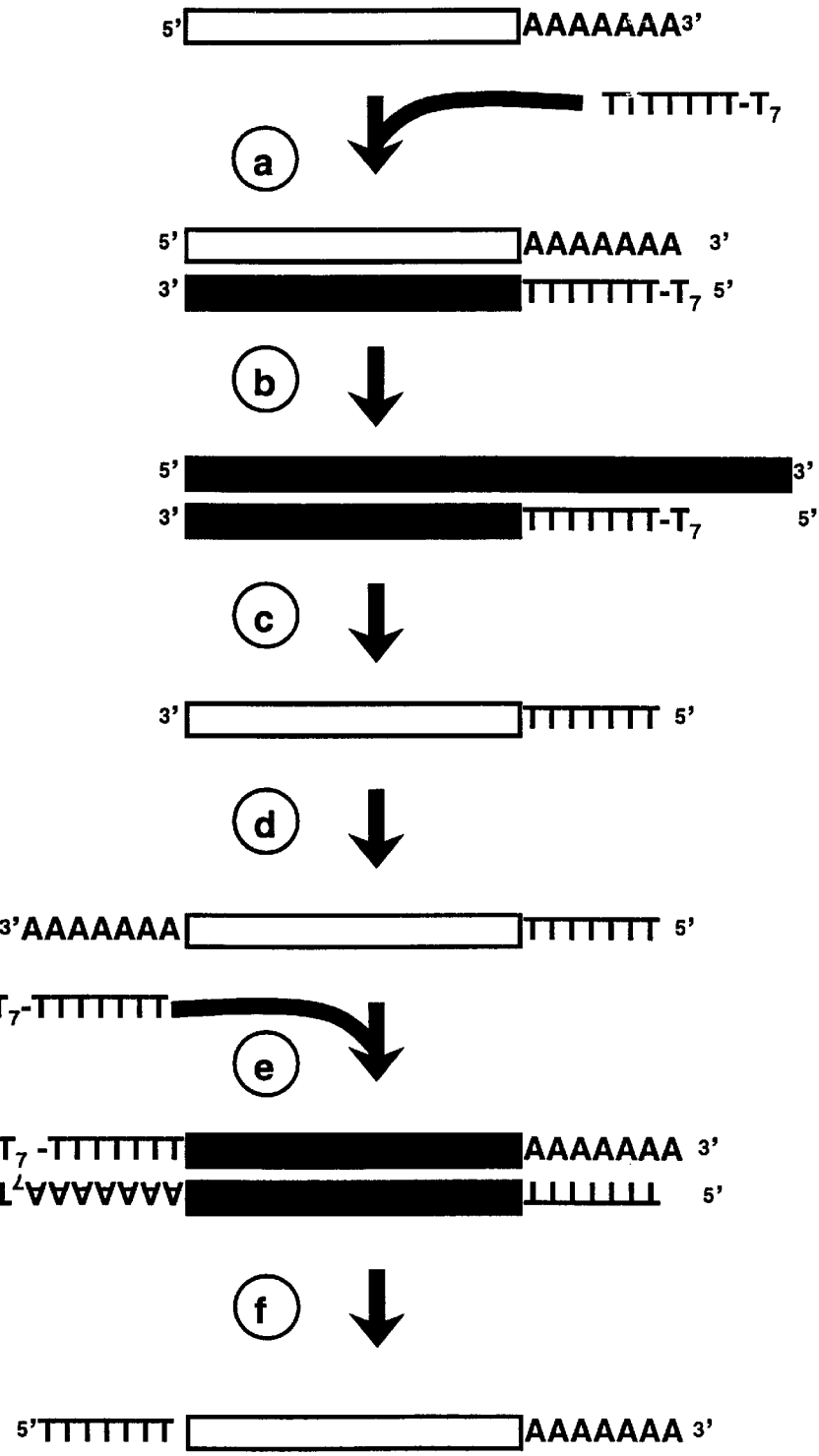
FIG. 1 is a schematic of one embodiment of the invention for amplifying mRNA.

In a more particular embodiment, the first RNA is itself made by amplifying an RNA, preferably a mRNA. For example, the first RNA may be made by amplifying a mRNA by the steps of hybridizing to the poly(A) tail of the mRNA a poly(T) oligonucleotide joined to an RNA polymerase promoter sequence, reverse transcribing the mRNA to form single-stranded cDNA, converting the single-stranded cDNA to a double-stranded cDNA and transcribing the double-stranded cDNA to form the first RNA. FIG. 1 is a schematic of this serial mRNA amplification embodiment of the invention, highlighting individual steps of the method:

(a) An oligonucleotide primer, consisting of 5'-$T_7$-RNA polymerase promoter-oligo $(dT)_{24}$-3', is annealed to the poly(A) tract present at the 3' end of mature mRNAs, and first-strand cDNA is synthesized using reverse transcriptase, yielding an RNA-DNA hybrid (RNA is denoted by open boxes; DNA by filled boxes); (b) The hybrid is treated with RNase H, DNA polymerase, and DNA ligase to convert the single-stranded cDNA into double-stranded cDNA;

(c) $T_7$ RNA polymerase is used to synthesize large amounts of amplified RNA (aRNA) from this cDNA. The incorporation of a modified $T_7$ polymerase promoter sequence into our primer, as compared to the altered promoter sequence utilized by Eberwine et al., PNAS 89: 3010–3014, 1992, greatly increases the yield of aRNA, (d) The aRNA is tailed with poly(A) using a poly(A) polymerase. This modification, generates much longer first-strand cDNA in the next step as compared to the original protocol;

(e) After denaturation and elimination of the aRNA, a $T_7$-RNA polymerase promoter-oligo (dT) primer is annealed to this newly synthesized poly(A) sequence, and reverse transcriptase is used to synthesize first-strand cDNA. Second-strand cDNA and the complementary strand of the polymerase promoter are synthesized as in (b); and (f) $T_7$ RNA polymerase is then used to generate aRNA from this cDNA template.

Another embodiment involves the incorporation of additional sequences during certain synthesis steps. These sequences allow, for example, for the PCR amplification of the amplified RNA, for direct second-round amplification without synthesizing a full second strand cDNA, etc. This embodiment is diagramed in FIG. 2:

(a) This is step (a) of FIG. 1, except that the primer for first strand cDNA synthesis also includes a promoter site for a different RNA polymerase (shown with $SP_6$; $T_3$ RNA polymerase site is also possible) between the poly(T) and the $T_7$ sequences;

(b) This is step (b) of FIG. 1;

(c) This is step (c) of FIG. 1, except that the aRNA now has an RNA polymerase site at its 5' end;

(d) This is step (d) of FIG. 1;

(e) This is step (e) of FIG. 1, except that the oligonucleotide used for priming first strand cDNA synthesis also has an additional sequence at its 5' end suitable for use as a priming site during polymerase chain reaction (PCR). Note also that the $SP_6$ or $T_3$ RNA polymerase site has been copied into first strand cDNA. Because this first strand cDNA has unique sequences at both its 5' and 3' ends, it can now be used directly in a PCR reaction for total amplification of all sequences, as an alternative to performing another round of aRNA synthesis;

(f) The first strand cDNA can be used directly for aRNA synthesis by annealing an oligonucleotide incorporating the complementary portion of the $SP_6$ or preferably, the $T_3$ RNA polymerase site. Or, the first strand cDNA can be converted into double-stranded cDNA through second strand synthesis, with aRNA synthesis then following.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for making a nucleic acid comprising the steps of adding a known nucleotide sequence to the 3' end of a first RNA having a known sequence at the 5' end to form a second RNA and reverse transcribing the second RNA to form a cDNA.

2. A method according to claim 1, wherein the adding step comprises contacting the first RNA with at least one of (a) a nucleotide and polyadenyltransferase and (b) an oligonucleotide and a ligase, whereby said polyadenyltransferase and/or said ligase adds said known nucleotide to the 3' end of said first RNA to form said second RNA.

3. A method according to claim 1, wherein the known sequence at the 3' end comprises, a poly(A) sequence.

4. A method according to claim 1, wherein the known sequence at the 5' end comprises at least one of (a) a poly(T) or poly(A) sequence and (b) an internal sequence of an mRNA or the complement thereof.

5. A method according to claim 1, wherein the known sequence at the 5' end comprise a poly(T) sequence and an RNA polymerase promoter sequence.

6. A method according to claim 1, wherein the known sequence at the 3' end comprises a poly(A) sequence and the reverse transcribing step is initiated at a noncovalently joined duplex region comprising a poly(T) sequence hybridized to the poly(A) sequence.

7. A method according to claim 1, wherein the known sequence at the 3' end comprises a poly(A) sequence and the reverse transcribing step is initiated at a noncovalently joined duplex region comprising a poly(T) sequence hybridized to the poly(A) sequence, wherein the poly(T) sequence is covalently joined to at least one of a RNA polymerase promoter sequence and a primer sequence.

8. A method according to claim 1, wherein the cDNA is single-stranded and isolated from the second RNA.

9. A method according to claim 1, wherein the cDNA is single-stranded and isolated from the second RNA by a method comprising the step of contacting the RNA with at least one of an RNase H, a denaturant, and an alkali.

10. A method according to claim 1, wherein the cDNA is single-stranded and converted to a double-stranded cDNA.

11. A method according to claim 1, wherein the cDNA is single-stranded and converted to a double-stranded cDNA and the conversion is initiated at a noncovalently joined duplex region.

12. A method according to claim 1, wherein the cDNA is single-stranded and converted to a double-stranded cDNA by a method comprising the steps of contacting the RNA with as RNase H and contacting the single-stranded cDNA with a DNA polymerase whereby the DNA polymerase initiates the conversion at a noncovalently joined duplex region.

13. A method according to claim 1, wherein the cDNA is single-stranded and converted to a double-stranded cDNA by a method comprising the steps of contacting the RNA with a denaturant and contacting the single-stranded cDNA with a DNA polymerase and an oligonucleotide primer comprising a sequence complementary to the 3' end of the single-stranded cDNA, whereby the DNA polymerase initiates the conversion at a noncovalently joined duplex region of the 3' end of the single-stranded cDNA and the oligonucleotide primer.

14. A method according to claim 1, wherein the cDNA is single-stranded and converted to a double-stranded cDNA by a method comprising the steps of contacting the RNA with a denaturant and contacting the single-stranded cDNA with a DNA polymerase and an oligonucleotide primer comprising a sequence complementary to the 3' end of the single-stranded cDNA and an RNA polymerase promoter, whereby the DNA polymerase initiates the conversion at a noncovalently joined duplex region of the 3' end of the single-stranded cDNA and the oligonucleotide primer.

15. A method according to claim 1, wherein the cDNA is single-stranded and converted to a double-stranded cDNA by a method comprising the steps of contacting the RNA with a denaturant and contacting the single-stranded cDNA with a DNA polymerase and an oligonucleotide primer comprising a sequence complementary to the 3' end of the single-stranded cDNA and an RNA polymerase promoter comprising a natural class III T7 RNA polymerase promoter sequence, whereby the DNA polymerase initiates the conversion at a noncovalently joined duplex region of the 3' end of the single-stranded cDNA and the oligonucleotide primer.

16. A method according to claim 1, wherein the cDNA is single-stranded and converted to a double-stranded cDNA by a method comprising the steps of contacting the RNA with a denaturant and contacting the single-stranded cDNA with a DNA polymerase and an at oligonucleotide primer comprising a sequence complementary to the 3' end of the single-stranded cDNA and an RNA polymerase promoter comprising SEQ ID NO:1 joined to an upstream flanking sequence of about 3 to 100 nucleotides, whereby the DNA polymerase initiates the conversion at a noncovalently joined duplex region of the 3' end of the single-stranded cDNA and the oligonucleotide primer.

17. A method according to claim 1, further comprising the step of repeatedly transcribing the cDNA to form a plurality of third RNAs.

18. A method according to claim 1, wherein the cDNA is single-stranded and converted to a double-stranded cDNA, and the method further comprises the step of repeatedly transcribing the double-stranded cDNA to form a plurality of third RNAs.

19. A method according to claim 1, wherein the first RNA is made by amplifying a mRNA.

20. A method according to claim 1, wherein the first RNA is made by amplifying a mRNA by the steps of hybridizing to the poly(A) tail of the mRNA a poly(T) oligonucleotide joined to an RNA polymerase promoter sequence, reverse transcribing the mRNA to form single-stranded cDNA, converting the single-stranded cDNA to a double-stranded cDNA and transcribing the double-stranded cDNA to form the first RNA.

21. A method according to claim 1, wherein the adding step comprises contacting the first RNA with a nucleotide and polyadenyltransferase.

* * * * *

```
                          SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:1:

TAATACGACT CACTATAGGG AGA                                              23

(2) INFORMATION FOR SEQ ID NO:2:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:2:

TAATACGACT CACTATAGGC GC                                               22

(2) INFORMATION FOR SEQ ID NO:3:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:3:

TAATACGACT CACTATAGGG CGA                                              23
```